(12) United States Patent
Wallace et al.

(10) Patent No.: US 7,336,985 B2
(45) Date of Patent: Feb. 26, 2008

(54) FETAL HEART RATE ELECTRODE ASSEMBLY, CONNECTOR FOR SAME, CABLE ASSEMBLY, SYSTEM, AND METHODS OF USE

(75) Inventors: Wm. Dean Wallace, Salt Lake City, UT (US); Richard A. Dixon, Bountiful, UT (US); Christopher A. Cutler, Centerville, UT (US); Steven R. Smith, Draper, UT (US)

(73) Assignee: Clinical Innovations, LLC, Lake Forest, IL (US)

( * ) Notice: Subject to any disclaimer, the term of this patent is extended or adjusted under 35 U.S.C. 154(b) by 448 days.

(21) Appl. No.: 10/956,176

(22) Filed: Sep. 30, 2004

(65) Prior Publication Data

US 2005/0137486 A1 Jun. 23, 2005

Related U.S. Application Data

(60) Provisional application No. 60/508,928, filed on Oct. 2, 2003.

(51) Int. Cl.
*A61B 5/0448* (2006.01)

(52) U.S. Cl. .................. 600/376; 600/511; 439/909

(58) Field of Classification Search ................ 600/376, 600/511

See application file for complete search history.

(56) References Cited

U.S. PATENT DOCUMENTS

| | | | |
|---|---|---|---|
| 3,827,428 A | 8/1974 | Hon et al. |
| 3,890,420 A | 6/1975 | Neward |
| 3,910,271 A | 10/1975 | Neward |
| RE28,990 E | 10/1976 | Hon et al. |
| 4,644,957 A | 2/1987 | Ricciardelli et al. |
| 4,686,996 A | 8/1987 | Ullbrich |
| 5,000,177 A | 3/1991 | Hoffmann et al. |
| 5,168,876 A | 12/1992 | Quedens et al. |
| 5,199,432 A | 4/1993 | Quedens et al. |
| 5,222,498 A | 6/1993 | Neward |

(Continued)

FOREIGN PATENT DOCUMENTS

EP 0 052 879 A 11/1981

(Continued)

OTHER PUBLICATIONS

International Search Report, Mar. 21, 2005, 7 pages.

*Primary Examiner*—Lee S. Cohen
(74) *Attorney, Agent, or Firm*—TraskBritt

(57) ABSTRACT

A fetal heart rate electrode assembly, a connector for use therewith and a cable assembly including a housing assembly configured for engagement with the connector. The electrode assembly includes a drive knob configured and located for selective extension of a fetal scalp electrode beyond a distal end thereof. The connector comprises a rotationally omnidirectional contact assembly disposed within a dielectric housing including an annular groove on the exterior thereof The housing assembly includes longitudinally resiliently biased pin contacts for end face contact with the contacts of the connector disposed within an inner housing of the housing assembly having an O-ring and an annular retention element positioned to respectively wipe the exterior of the connector housing and grasp the connector housing at the annular groove when the connector is inserted thereinto. A system and methods of use are also disclosed.

17 Claims, 6 Drawing Sheets

U.S. PATENT DOCUMENTS

| | | |
|---|---|---|
| 5,277,613 A | 1/1994 | Neward |
| 5,345,935 A | 9/1994 | Hirsch et al. |
| 5,373,843 A | 12/1994 | Quedens et al. |
| 5,377,677 A * | 1/1995 | Dowd et al. .................. 600/376 |
| 5,632,274 A | 5/1997 | Quedens et al. |
| 5,634,459 A | 6/1997 | Gardosi |
| 5,671,736 A | 9/1997 | Pettit et al. |
| 5,680,859 A | 10/1997 | Urion et al. |
| 6,039,685 A | 3/2000 | Bushek |
| 6,115,624 A * | 9/2000 | Lewis et al. .................. 600/376 |
| 6,151,520 A | 11/2000 | Combs |
| 6,292,679 B1 | 9/2001 | Sheard |
| 6,321,103 B1 | 11/2001 | Dowd et al. |
| 6,356,778 B1 | 3/2002 | Pirc |
| 6,363,272 B1 * | 3/2002 | Combs .................. 600/376 |
| 2003/0045911 A1 | 3/2003 | Bruchmann et al. |

FOREIGN PATENT DOCUMENTS

| | | |
|---|---|---|
| EP | 0 484 107 A1 | 10/1991 |
| EP | 0 770 350 A2 | 10/1996 |

\* cited by examiner

FETAL HEART RATE ELECTRODE ASSEMBLY, CONNECTOR FOR SAME, CABLE ASSEMBLY, SYSTEM, AND METHODS OF USE

RELATED APPLICATIONS

This application claims the benefit of U.S. Provisional Patent Application Ser. No. 60/508,928, filed Oct. 2, 2003 and entitled "FETAL HEART RATE AND CONNECTOR MONITORING SYSTEM," the disclosure of which is incorporated herein by reference.

BACKGROUND OF THE INVENTION

Field of the Invention: The present invention relates to fetal heart rate monitoring using fetal scalp electrodes. More particularly, the present invention relates to a disposable fetal scalp electrode assembly including a connector, a reusable cable assembly configured for cooperatively engaging the connector, a system including the fetal heart rate electrode assembly and the reusable cable assembly, and methods of use.

State of the Art: Fetal heart rate monitoring during labor has been an accepted medical practice for decades. The most favored techniques are those which employ an electrode in contact with the fetus.

One noteworthy apparatus for effecting such fetal contact is disclosed in U.S. Pat. No. 3,827,428 (Re 28,990) to Hon et al., the disclosure of which is incorporated herein by reference. In the Hon apparatus, a first, spiral electrode is carried at the distal end of a drive tube slidingly received within a larger diameter guide tube, the first, spiral electrode being located initially within the distal end of the guide tube. A second, reference electrode is longitudinally dielectrically isolated and spaced from the first electrode, and each electrode is connected to a wire of a twisted wire pair running proximally within the guide tube. A physician inserts the distal end of the guide tube within the mother's vagina and cervix until the distal end of the guide tube makes contact with the head of the fetus. The drive tube is then extended distally so as to advance the end of the first, spiral electrode beyond the end of the guide tube and into contact with the epidermis of the head of the fetus. The drive tube is then rotated to screw the first, spiral electrode into the epidermis. The drive tube and surrounding guide tube are then withdrawn, leaving the first, spiral electrode attached to the fetal epidermis, the second, reference electrode in contact with the vaginal and cervical secretions of the mother. The proximal ends of each wire of the wire pair are then attached to a monitoring device. Further developments in this general type of apparatus are disclosed in U.S. Pat. Nos. 3,890,420, 3,910,271, 5,222,498 and 5,277,613, all to Neward, U.S. Pat. No. 5,671,736 to Pettit et al., and U.S. Pat. No. 5,680,859 to Urion et al., the disclosures of each of which are incorporated herein by reference.

It was recognized in U.S. Pat. No. 5,168,876 to Quedens et al., the disclosure of which is hereby incorporated by reference, that it would be desirable to employ a connector and circuit board assembly in the form of a reusable coupling device cooperatively configured to engage a connector at the proximal ends of the twisted wire pair located between the proximal ends of the twisted wire pair and the monitor. In Quedens, the proximal ends of the twisted wire pair are configured with a plug-type connector which is inserted into the connector of the coupling device, another cable then extending from the latter to a monitor. It was recognized in U.S. Pat. No. 5,199,432 to Quedens et al., the disclosure of which is hereby incorporated by reference, that it would be desirable to fabricate the connector at the proximal end of the twisted wire pair to be smaller in lateral dimension than the inner diameter of the drive tube, to facilitate withdrawal of the drive tube and guide tube thereover. Various connector contact configurations are disclosed in U.S. Pat. Nos. 5,373,843 and 5,632,274 to Quedens et al., U.S. Pat. No. 6,151,520 to Combs, U.S. Pat. No. 6,321,103 to Dowd et al. and U.S. Pat. No. 6,356,778 to Pirc, the disclosures of each of which are hereby incorporated by reference.

While the foregoing patents disclose various improvements in the state of the art, there remain a number of deficiencies with respect to the fetal scalp electrode assembly including a connector associated with the twisted wire pair, as well as to cooperatively configured coupling devices for receiving the connector.

BRIEF SUMMARY OF THE INVENTION

The present invention, in a number of embodiments, includes a fetal heart rate electrode assembly including a connector, a cable assembly configured for cooperatively engaging the connector, a system including the fetal heart rate electrode assembly and the cable assembly, and methods of use.

An exemplary embodiment comprises a fetal heart rate electrode assembly. The fetal heart rate electrode assembly may include a spiral electrode or, in alternative electrode structure, a suction vacuum cup with a surface electrode extending distally from a dielectric electrode block.

In the case of the fetal heart rate electrode assembly employing a spiral electrode, a reference electrode is located close to, but electrically isolated from, the spiral electrode and is also carried by the electrode block. The spiral electrode may be formed of stainless steel, and be gold plated. One wire of a twisted wire pair is coupled to the spiral electrode and the other wire to the reference electrode, the twisted wire pair extending proximally within a drive tube to a connector of smaller lateral dimension than the inner diameter of the drive tube. The electrode block and the distal end of the drive tube are of similar outer diameter and are cooperatively configured so that rotation of the drive tube will effect rotation of the electrode block and, so, of the spiral electrode. The drive tube is received within a larger diameter guide tube, which may, optionally be preformed into an arcuate shape. The electrode block is also received within the guide tube. A drive knob comprising a body having a distal bore of a diameter to snugly receive the proximal end of the drive tube, an annular stop of lesser diameter and a proximal bore having a slot opening thereinto through the side wall of the drive knob is disposed over the distal end of the drive tube. The drive knob further includes a longitudinally extending stop tab having a foot at a distal, free end thereof disposed at the distal end of the body, the stop tab being resiliently biased to extend away from the axis of the drive knob at an acute angle and including a distally facing abutment at the heel of the foot. The stop tab is dimensioned, in combination with a length of the drive tube, to maintain the electrode block and spiral electrode within the guide tube when the foot is inserted between the exterior of the drive tube and the interior of the guide tube. If the drive tube is withdrawn proximally to release the foot, the drive tube may then be subsequently advanced distally through the guide tube to expose the spiral electrode, distal travel thereof beyond the end of the guide tube being limited by abutment of the proximal end of the body with the distal end of the guide tube. Thus, the spiral electrode may be precluded from inadvertent extension beyond the distal end of the guide tube during shipping of the fetal heart rate electrode assembly, as well as during insertion thereof into the vagina and cervix of a pregnant woman during labor.

A suction vacuum cup-type fetal heart rate electrode assembly is disclosed in U.S. Pat. No. 5,345,935 to Hirsch et al., the disclosure of which is incorporated herein in its entirety by reference. A commercial version of such a device is offered by Clinical Innovation Associates, Inc., d/b/a Clinical Innovations of Murray, Utah, as the SoftBeat™ fetal heart rate electrode assembly. In such a device, the suction electrode may be formed of a carbon conductive plastic. The suction vacuum cup-type fetal heart rate electrode assembly may employ a connector according to the present invention in association with a cable assembly according to the present invention.

Another exemplary embodiment comprises a compact, rotationally omnidirectional connector that may be employed with a fetal heart rate electrode assembly such as, for example, a fetal heart rate electrode assembly as described herein. The rotationally omnidirectional connector comprises a central contact provided by one wire of a pair of wires, an annular dielectric material disposed thereabout and an annular contact substantially concentrically encompassing the central contact and connected to another wire of the pair of wires. End faces of the first and second contacts may be substantially coplanar and perpendicular to a longitudinal axis of the connector. The end faces are longitudinally recessed within a cavity at an end of the connector provided by a substantially cylindrical, dielectric end portion of the connector, which includes an annular recess on the exterior thereof remote from the end of the connector. When used with a fetal heart rate electrode assembly having a drive tube and a guide tube as described herein, the connector may be of diminutive size so as to pass through the drive tube while providing low cost, yet robust, electrical contact capability due to the end face contact approach employed.

Yet another exemplary embodiment comprises a cable assembly configured for engaging the above-described rotationally omnidirectional connector. The reusable cable assembly comprises a housing assembly including an outer housing configured to receive a smaller, inner housing proximate one end of the outer housing, the inner and outer housings being cooperatively configured for receipt of a connector end thereinto at the one end. The inner housing includes two annular, coaxially aligned and longitudinally spaced recesses coaxially aligned with and inwardly disposed from an aperture through which an end portion of a connector may be received. The outer annular recess holds an elastomeric 0-ring sized for resilient radial engagement with the exterior of the connector end portion when inserted therethrough, while the innermost recess holds an element formed in a substantially annular configuration and sized and configured for resilient radial engagement with an annular recess on the connector end portion. The inner and outer housings further comprise cooperative apertures extending through the side walls thereof from the exterior of the outer housing to the interior of the inner housing. A plug carried on the outer housing is sized and configured for selective closure of the inner housing aperture. Ends of two longitudinally resiliently biased pin contacts disposed within the inner housing extend through a wall thereof in fluid-tight fashion into an interior of the outer housing, where they are connected to wires of a cable extending into the outer housing. Opposing ends of the two pin contacts are located and oriented for face contact with, respectively, end faces of a central contact and an annular contact of a connector end portion. The inner housing is configured to constrain any significant lateral deviation of the two pin contacts to ensure precise contact with the end faces of the connector contacts. The two pin contacts may comprise gold-plated stainless steel for corrosion prevention and to facilitate soldering thereof to wires of the cable and, further, may be dielectrically coated over major medial portions thereof, leaving the ends exposed.

As described above, the inner housing is configured to provide a chamber sealed from the rest of the outer housing interior outside of the inner housing, so that the connector may still function after exposure to a fluid entering the chamber of the inner housing, since the remainder of the interior of the outer housing, housing the connections of the pin contacts to the cable wires, remains sealed. Further, the side wall aperture of the inner housing, in combination with the plug, provides a wash-out port wherein any debris, such as mucous, vernix and blood (clotted or not) which may enter the chamber of the inner housing may be flushed therefrom and from the vicinity of the pin contacts. The presence of the 0-ring reduces the incidence of entry of such debris into the interior of the inner housing, while resilient engagement of the annular element with the connector end portion recess retains the connector within the inner housing in resiliently biased contact with the pin contacts (which are longitudinally resilient loaded by disposition of the connector thereagainst) and provides a positive tactile "feel" that the connector is properly seated within the housing assembly. The use of a central contact and coaxial annular contact with the connector of the present invention in combination with longitudinally biased pins contacting the end faces thereof advantageously provides a rotationally omnidirectional connection capability. Notably, the configuration of the pins in combination with supporting structure of the inner housing may be used to provide resiliency, reducing any tendency of the contact pins to stick or jam in their longitudinal travel.

A further exemplary embodiment of the present invention comprises a combination of the above-described connector and cable assembly.

A still further exemplary embodiment of the present invention comprises a fetal heart rate monitoring system including a fetal heart rate electrode assembly with a rotationally omnidirectional connector, a cable assembly configured for engaging the connector, and a monitor.

A still further exemplary embodiment comprises a method of use of a fetal heart rate electrode assembly according to the present invention, a method of use of a rotationally omnidirectional connector in combination with a cable assembly according to the present invention, and a method of use of the cable assembly.

In the exemplary embodiments of the present invention, the fetal heart rate electrode assembly is disclosed as a disposable structure, while the cable assembly is disclosed as a reusable structure and, accordingly, the components and materials of each are accordingly structured and fabricated. However, the invention is not so limited.

The features, elements and advantages of the present invention will be apparent to those of ordinary skill in the art from a consideration of the following detailed description taken in combination with the accompanying drawings.

BRIEF DESCRIPTION OF THE SEVERAL VIEWS OF THE DRAWINGS

In the drawings, which illustrate what is currently considered to be the best mode for carrying out the invention and in which like elements and features are identified by like reference numerals:

FIG. 1A comprises an enlarged view of the distal end of the fetal heart rate electrode assembly of FIG. 1;

FIG. 1B comprises an enlarged, side-sectional elevation of a drive knob used with the fetal heart rate electrode assembly of FIG. 1;

FIG. 1C comprises an enlarged, partial sectional side elevation of a connector according to the present invention and incorporated in the fetal heart rate electrode assembly of FIG. 1;

FIG. 1D is an end view of the connector of FIG. 1C depicting the contacts thereof;

DETAILED DESCRIPTION OF THE INVENTION

The present invention, in a number of embodiments, includes a fetal heart rate electrode assembly including a connector, a cable assembly configured for cooperatively engaging the connector, a system including the fetal heart rate electrode assembly and the cable assembly, and methods of use.

Figure 1:
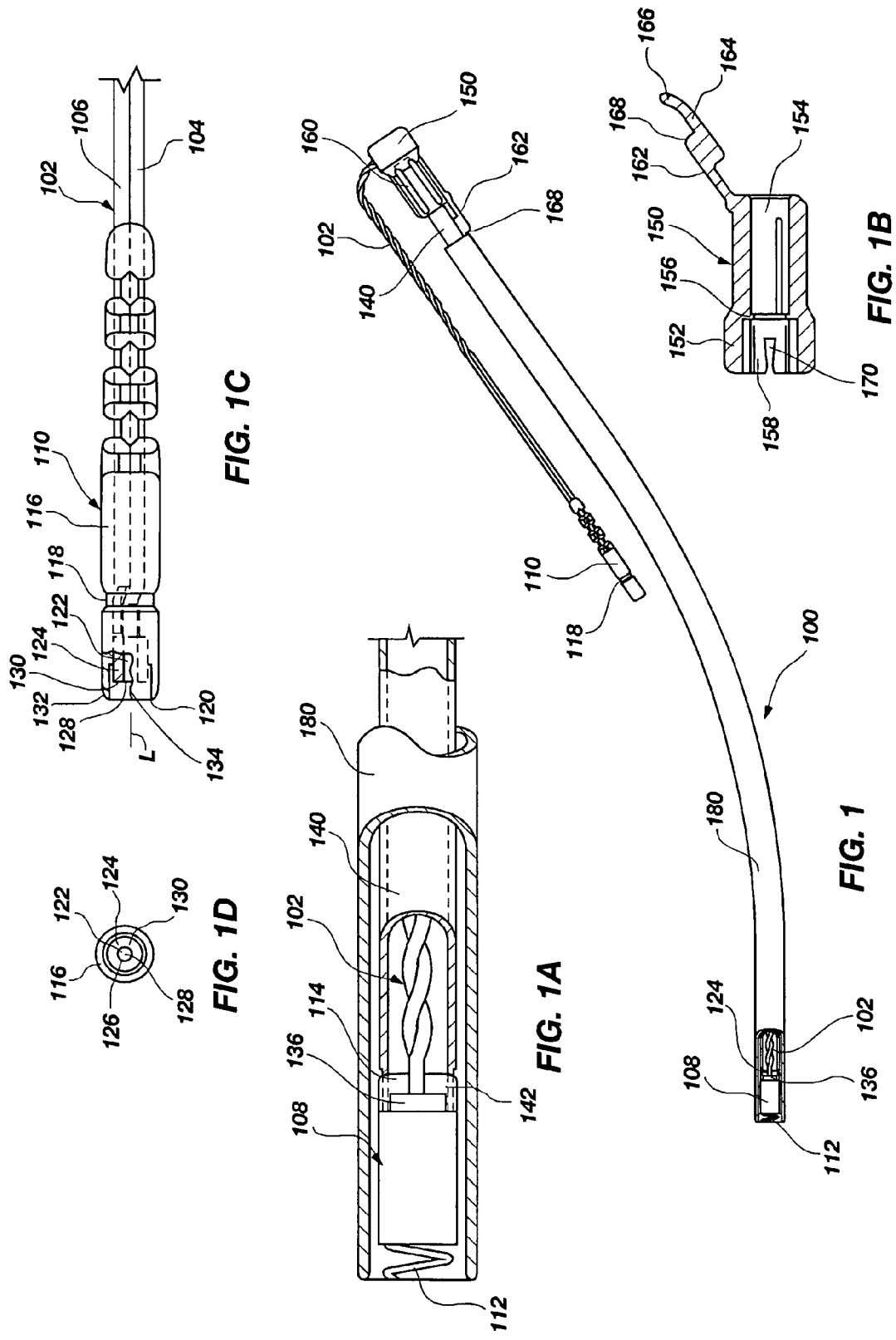
FIG. 1 comprises a side-sectional elevation of an exemplary fetal heart rate electrode assembly according to the present invention.

Referring now to FIGS. 1 through 1D, an exemplary embodiment of a fetal heart rate electrode assembly 100 of the present invention will be described. The fetal heart rate electrode assembly 100 comprises a twisted wire pair 102 comprising a first insulated wire 104 and a second insulated wire 106 which extend at one end thereof, which will be termed the distal end, to an electrode block 108 and at an opposing end thereof, which will be termed the proximal end 120, to a connector 110. The terms "distal" and "proximal" as referenced herein indicate proximity to the clinician and remoteness to the clinician (and, thus, proximity to the patient). Wires 104 and 106 may comprise copper with a polyvinyl chloride (PVC) dielectric jacket.

Electrode block 108 may comprise a molded polypropylene body, which carries a first, spiral electrode 112 extending from the distal end of electrode block 108 and having a needle point thereon for piercing the fetal scalp and a second, reference electrode 114 in the form of a plate disposed diametrically across the electrode block 108 and protrudes proximally therefrom. Spiral electrode 112 and reference electrode 114 may be formed from stainless steel, and be plated with gold for corrosion resistance and to facilitate soldering thereof respectively to wires 104 and 106.

Connector 110 comprises an overmolded dielectric body 116 which may be formed of polypropylene. The proximal end portion of dielectric body 116 is substantially cylindrical and includes an annular recess 118 therein extending thereabout in axially spaced relationship to proximal end 120, annular recess 118 being entirely defined by dielectric material. A central contact 122 of connector 110 is provided by a proximal end of wire 104, insulation 126 thereon extending to the proximal end 120, while an annular contact 124 is provided by a tubular body which may be formed of brass with a gold flash finish to facilitate soldering of wire 106 thereto. Annular contact 124 is disposed coaxially about central contact 122 with insulation 126 of wire 104 disposed therebetween. The respective proximal, exposed end faces 128 and 130 of central contact 122 and annular contact 124 may be substantially coplanar and perpendicular to the longitudinal axis L of connector 110. This arrangement provides a rotationally omnidirectional contact capability when longitudinally aligned pin contacts of a cooperatively configured housing assembly of a cable assembly, as described in detail below, are employed. Dielectric body 116 extends proximally beyond the exposed end faces 128 and 130 of central and annular contacts 122 and 124, respectively, forming a skirt 132 which defines a cavity 134, the end of skirt 132 being tapered to facilitate insertion of connector 110 into a housing assembly of the aforementioned cooperatively configured housing assembly of the cable assembly. The distal end of dielectric body 116 of connector 110 may be segmented, as shown, for flexibility.

The fetal heart rate electrode assembly 100 further comprises a drive tube 140 of substantially the same outer diameter as electrode block 108. The distal end of drive tube 140 may be formed of polypropylene or polyethylene and includes diametrically opposing, axially extending slots 142, which receive the laterally outer edges of proximally protruding portion of reference electrode 114, the distal end of drive tube 140 extending over a proximal, reduced diameter portion 136 of electrode block 108. This arrangement enables rotation of electrode block 108 when a first, spiral electrode is to be inserted in the fetal scalp.

Twisted wire pair 102 extends proximally through drive tube 140 and out the proximal end 120 thereof, which is capped by drive knob 150. Drive knob 150 comprises a molded dielectric drive knob body 152 formed, for example, of polypropylene or polyethylene. Drive knob body 152 comprises a distal bore 154 of substantially the same inner diameter as the outer diameter of drive tube 140, distal bore 154 terminating at an annular stop 156 protruding radially inwardly to define a diameter substantially the same as the inner diameter of drive tube 140. Distal bore 154 may, optionally, include a plurality of longitudinally extending, radially inwardly protruding ridges (one shown in FIG. 1B) to provide an interference fit for the proximal end of drive tube 140 when the latter is inserted into distal bore 154. Proximal bore 158 of larger diameter than distal bore 154 extends from annular stop 156 to the distal end of drive knob body 152, which is of enlarged outer diameter and may include ridges 160 thereon. A stop tab 162 extends distally from drive knob body 152, and may be integrally formed therewith from an elastomeric material so as to provide a resilient bias thereto. As depicted in FIG. 1B, stop tab 162 is disposed at an acute angle to the longitudinal axis of drive knob body 152, and includes a foot 164 having a toe 166 extending distally at an acute angle to toe 166, toe 166 being resiliently biased with respect to foot 164. Stop tab 162 further includes a distally facing abutment 168 at the heel of foot 164. Drive knob 150 is disposed over and bonded to the proximal end of drive tube 140. Twisted wire pair 102 extends therethrough and through an axially extending slot 170 extending through the side wall of drive knob 152, connector 110 lying there beyond.

Guide tube 180, which may be formed of polypropylene or polyethylene, has an inner diameter somewhat larger than the outer diameter of drive tube 140 and electrode block 108 so as to permit rotation of those two components via rotational manipulation of drive knob 150. Guide tube 180 may be preformed into an arcuate shape, or may be flexible to permit bending thereof to such a shape during use. For shipping and during initial insertion of fetal heart rate electrode assembly 100 into a pregnant woman's vagina and cervix, the distal end of drive tube 140 with electrode block 108 and distally extending spiral electrode 112 are maintained within guide tube 180. The proximal end of drive tube 140 with attached drive knob 150 protrudes beyond the proximal end of guide tube 180. Foot 164 of stop tab 162 is inserted into the annulus between guide tube 180 and drive tube 140, the resiliency of stop tab 162 and that of toe 166 maintaining the drive tube 140 in position against proximal withdrawal from guide tube 180. Distally facing abutment 168 prevents drive tube 140 and, thus, electrode block 108 and distally extending spiral electrode 112 from being extended beyond the distal end of guide tube 180 during shipping and insertion into a patient's vagina and cervix. After such insertion, drive tube 140 may be proximally withdrawn sufficiently to release stop tab 162 and then extended distally through guide tube 180 to expose electrode block 108 and spiral electrode 112 for contact with the fetal scalp. The distal end of drive knob body 152 limits the longitudinal extension of electrode block 108 and spiral electrode 112 to a predetermined travel.

Figure 2:
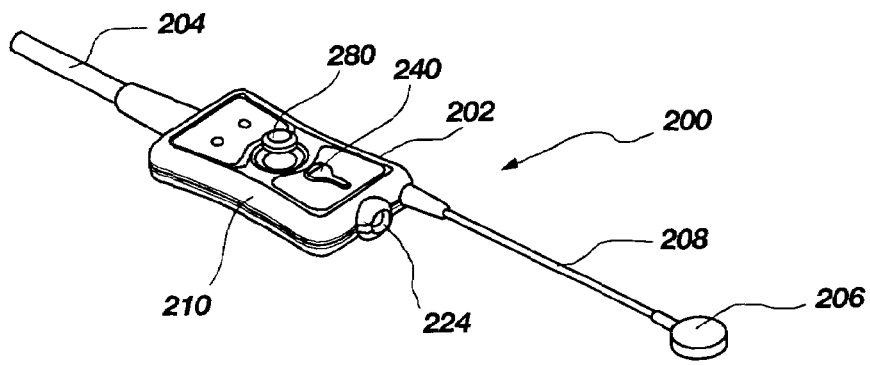
FIG. 2 is a perspective view of one variant of an exemplary cable assembly according to the present invention having a maternal reference electrode seat placed on a cable extending therefrom.

Referring now to FIGS. 2 through 6, an exemplary embodiment of a cable assembly 200 according to the present invention will be described. Referring to FIGS. 2 and 3B, cable assembly 200 comprises a housing assembly 202 having a multi-conductor cable 204 extending therefrom and, optionally, a maternal reference electrode seat 206, to which a disposable electrode (not shown) may be operably coupled, at the end of a single wire cable 208. FIG. 3A depicts another variant of cable assembly 200 wherein housing assembly 202 carries an integral maternal reference electrode seat 206 on the underside thereof in fluid-tight, sealed relationship thereto. A suitably configured connector (not shown) is disposed at the end of multi-conductor cable 204 distal from housing assembly 202 for connection to a monitor (not shown, see FIG. 7) for monitoring fetal heart rate.

Figure 3A:
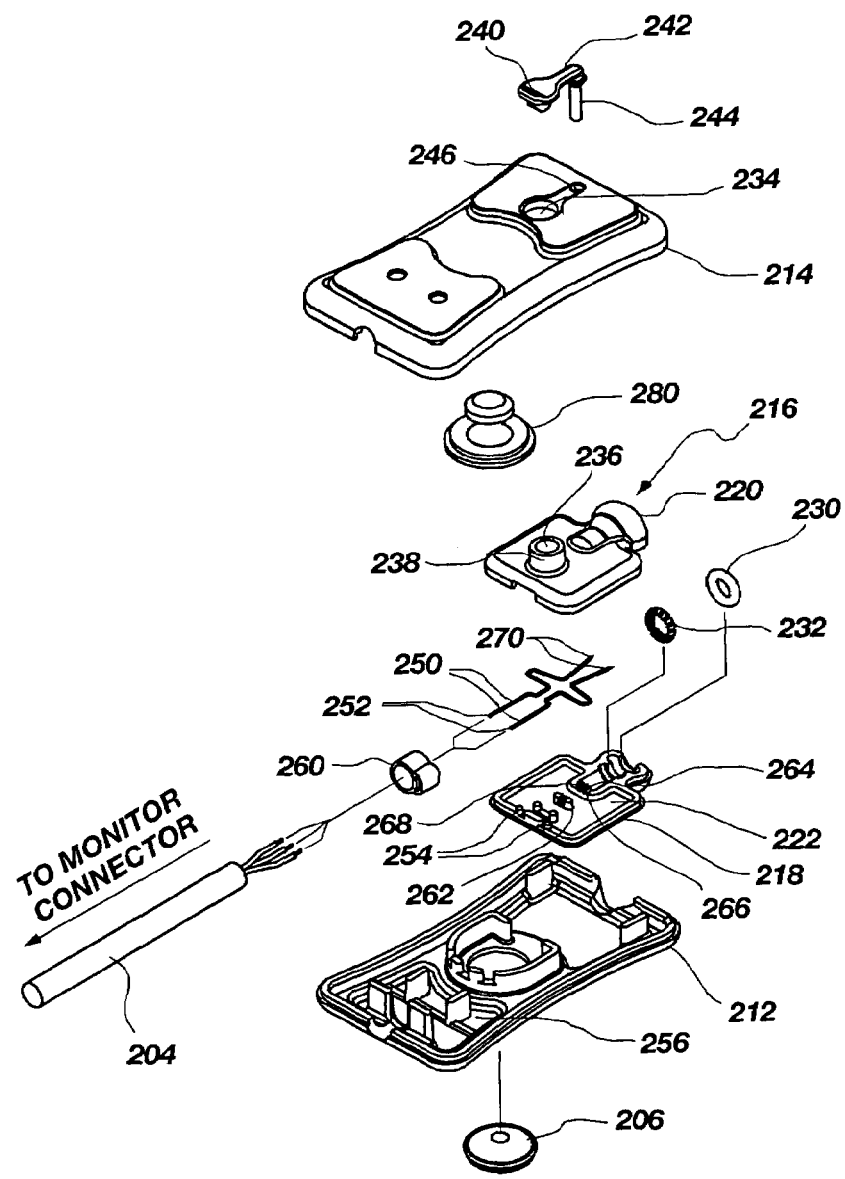
FIG. 3A is an exploded view of another variant of an exemplary cable assembly according to the present invention having an integral maternal reference electrode seat.
Figure 3B:
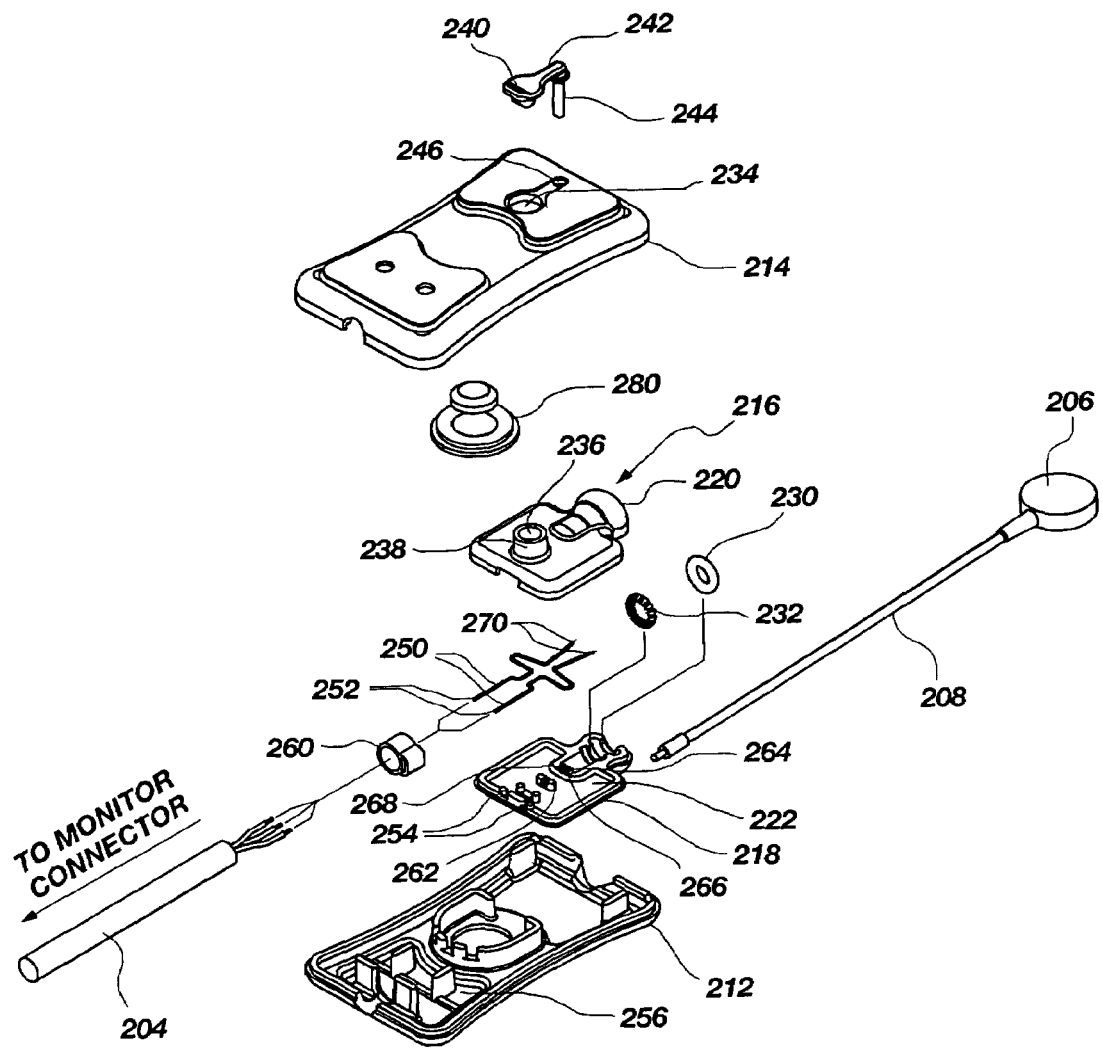
FIG. 3B is an exploded perspective view of the exemplary cable assembly of FIG. 2.
Figure 4:
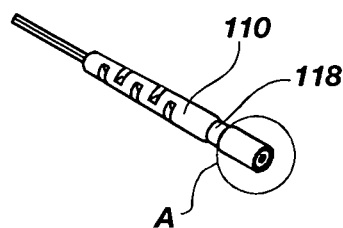
FIG. 4 is a perspective view of an exemplary connector of the configuration depicted in FIGS. 1C and 1D.
Figure 4A:
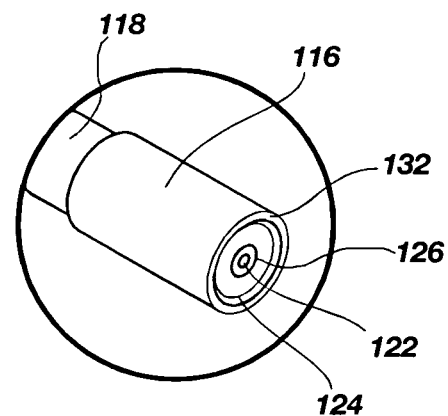
FIG. 4A is an enlarged view of the end of the connector of FIG. 4 in the circle denoted A thereon.

Referring now to FIGS. 3A and 3B, both variants of housing assembly 202 comprise an outer housing 210 including mating outer housing segments 212 and 214, within which is disposed a smaller, inner housing 216 including mating inner housing segments 218 and 220. Inner housing segments 218 and 220, when assembled, define a chamber 222 having an aperture 224 (FIGS. 5A and 5B) opening thereinto for insertion of connector 110. Inner housing 216 may be assembled to include the various components described below, inner housing segments 218 and 220 bonded together using, for example, an ultraviolet (UV)-sensitive adhesive, inner housing 216 then being placed within housing segment 212 of outer housing 210 along with the end of multi-conductor cable 204, and housing assembly 202 completed.

The inner housing 216 includes two annular, coaxially aligned and longitudinally spaced recesses 226 and 228 (FIGS. 5A and 5B) coaxially aligned with and inwardly disposed from aperture 224 through which an end portion of a connector 110 may be received. The outer annular recess 226 holds an elastomeric annular element in the form of O-ring 230 sized for resilient radial engagement with the exterior of the connector 110 end portion when inserted therethrough, while the innermost recess 228 holds an annular element comprising a coil spring 232 formed in a substantially annular configuration (commercially known as a "Bal-Spring") and sized and configured for resilient radial engagement with annular recess 118 on the proximal end portion, also termed the "presenting portion," of dielectric body 116 of connector 110. The outer and inner housings 210 and 216 further comprise respective, cooperative apertures 234, 236 extending through the side walls thereof from the exterior of the outer housing 210 to the interior of the inner housing 216. Aperture 236 is defined by a tubular projection 238 which extends into aperture 234 and which is sealed against the inner boundary thereof. An elastomeric plug 240 carried on the outer housing 210 by a tab 242 extending to a base 244 inserted in outer housing aperture 246 is sized and configured for selective closure of the aperture 236 of inner housing 216. Ends 252 of two longitudinally resiliently biased pin contacts 250 disposed within the inner housing 216 extend through a wall thereof at extension point 254 in fluid-tight fashion (due to the bonding together of inner housing segments 218 and 220) into an interior 256 of outer housing 210, where they are connected to wires of multi-conductor cable 204 extending into the outer housing 210, multi-conductor cable 204 being physically secured within outer housing 210 by clamp 260. Opposing ends of the two pin contacts 250 are located and oriented within chamber 222 for face contact with, respectively, end faces 128 and 130 of central contact 122 and annular contact 124 of connector 110. The inner housing 216, and specifically inner housing segment 218, is configured with alignment projections 262 and 264 comprising, for example, teeth 266 with gaps 268 therebetween to receive pin contacts 250 (see FIGS. 5A and 5B) constrain any significant lateral deviation of the portions thereof longitudinally aligned with aperture 224 to ensure precise contact with the end faces 128 and 130 of the connector 110 central and annular contacts 122 and 124, respectively. Inner housing segment 220 of inner housing 216 is cooperatively configured with alignment projections 262 and 264 including teeth 266 (not shown) which protrude into gaps 268 to provide additional constraint against all but longitudinal motion of pin contacts 250. Pin contacts 250 may comprise gold-plated stainless steel for corrosion prevention and to facilitate soldering thereof to wires of the multi-conductor cable 204 and, further, may be dielectrically coated over major medial portions thereof as with a Parylene™ polymer, leaving the-ends ends 252 exposed. The tips 270 of pin contacts 250 may be sharp and needle-like. In the exemplary embodiment, pin contacts 250 are configured as leaf springs which flex, under constraint of alignment projection 262 and retention bosses 272 (FIGS. 5A and 8B'), responsive to insertion of a connector 110 into aperture 224 and into contact with pin contacts 250, to provide a positive, longitudinal resilient bias for tips 270 thereof.

As described above, the inner housing 216 is configured to provide a chamber 222 sealed from the rest of the interior 256 of outer housing 210, so that the housing assembly 202 may still function after submersion, for example due to fluid being spilled thereon, or flushing as described below. In either instance, only chamber 222 housing pin contacts 250 would be exposed to the fluid, the remainder of the interior of housing assembly 202 remaining isolated from the fluid. Further, the side wall aperture 236 of the inner housing 216, in combination with the plug 240, provides a wash-out port wherein any debris, such as mucous, vernix and blood (clotted or not) which may enter the chamber 222 of the inner housing 216 may be flushed therefrom and from the vicinity of the pin contacts 250. The presence of the O-ring 230 reduces the incidence of entry of such debris into the interior of inner housing 210, while resilient engagement of the annular element O-ring 230 comprising coil spring 232 with the connector 110 end portion annular recess 118 retains the connector 110 within the inner housing 216 in resiliently biased contact with the pin contacts 250 (which are longitudinally resiliently loaded by disposition of the connector 110 thereagainst) and provides a positive tactile "feel" that the connector 110 is properly seated within the housing assembly 202. The use of a central contact 122 and coaxial annular contact 124 with the connector 110 of the present invention in combination with longitudinally biased pin contacts 250 contacting the end faces 128, 130 thereof advantageously provides a rotationally omnidirectional connection capability. Notably, the configuration of the pin contacts 250 in combination with supporting structure of the inner housing 216 may be used to provide resiliency, reducing any tendency of the pin contacts 250 to stick or jam in their longitudinal travel.

It is also noted that outer housing 210 may include knob 280 to facilitate connection of housing assembly 202 to a retention strap placed, for example, on the leg of a patient. It is further noted that the maternal reference electrode seat 206 which in the exemplary embodiment of FIG. 3B is connected, as by soldering of the wire of single wire cable 208 to a wire of multi-conductor cable 204, may be incorporated in housing assembly 202 as depicted in the embodiment of FIG. 3A. Optionally, two such maternal reference electrode seats may be incorporated with cable assembly 200. Further, a maternal reference electrode is not a requirement of the present invention. Various monitors of different manufacture may or may not be adapted to receive signals from such maternal reference electrode seats, and the cable assembly 200, as well as fetal heart rate electrode assembly 100 of the present invention, are suitable for use with monitors from any source when appropriately configured, with or without the maternal reference electrode seats.

Figure 5:
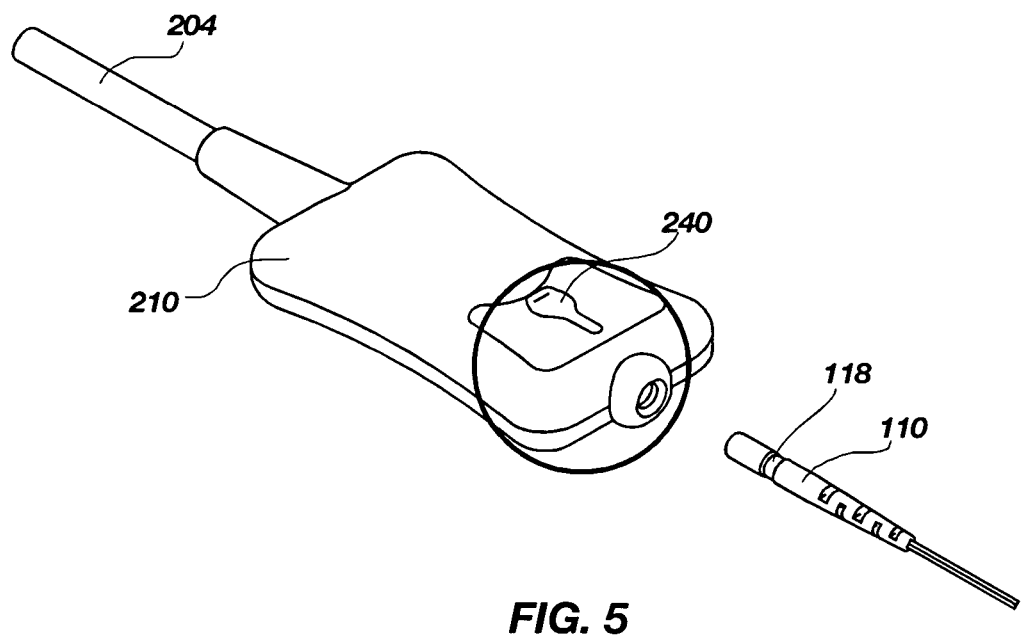
FIG. 5 is a perspective view of a housing assembly of a cable assembly according to the present invention similar to that depicted in FIG. 2, but without a maternal reference electrode seat and with the connector as depicted in FIG. 4 aligned for engagement therewith.
Figure 5A:
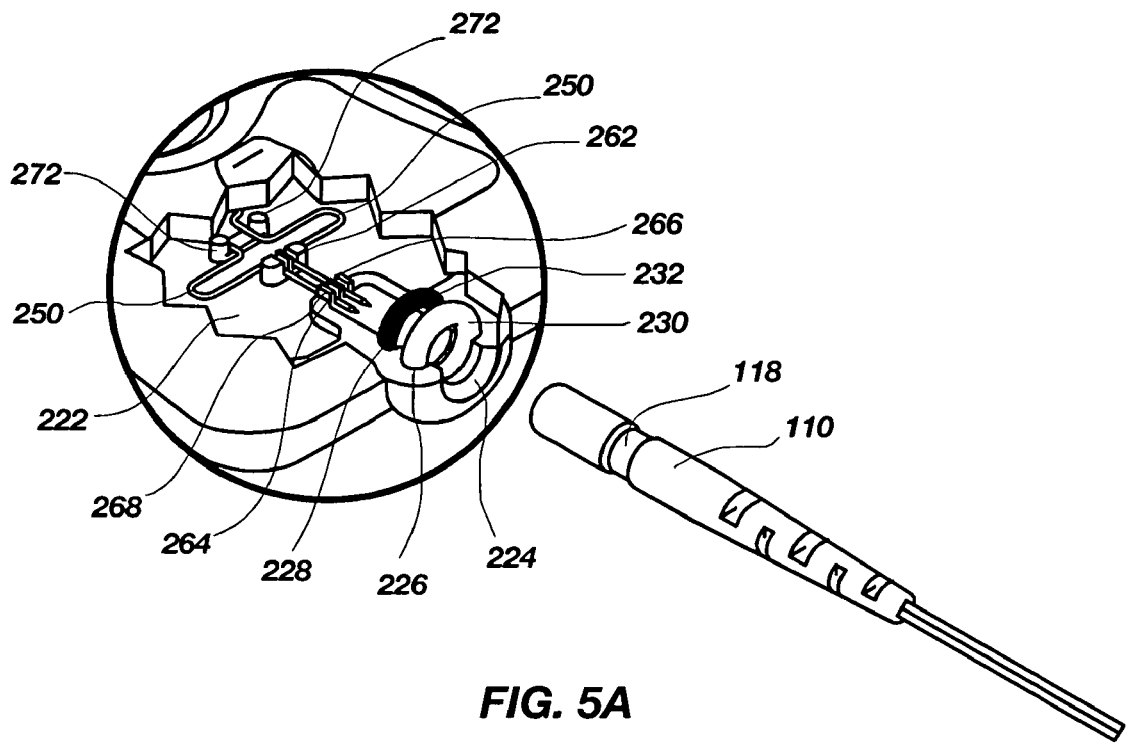
FIG. 5A is an enlarged, partial cutaway perspective view of a portion of the housing assembly depicted in FIG. 5 in the circle thereon with the connector as depicted in FIG. 4 aligned for engagement therewith.
Figure 5B:
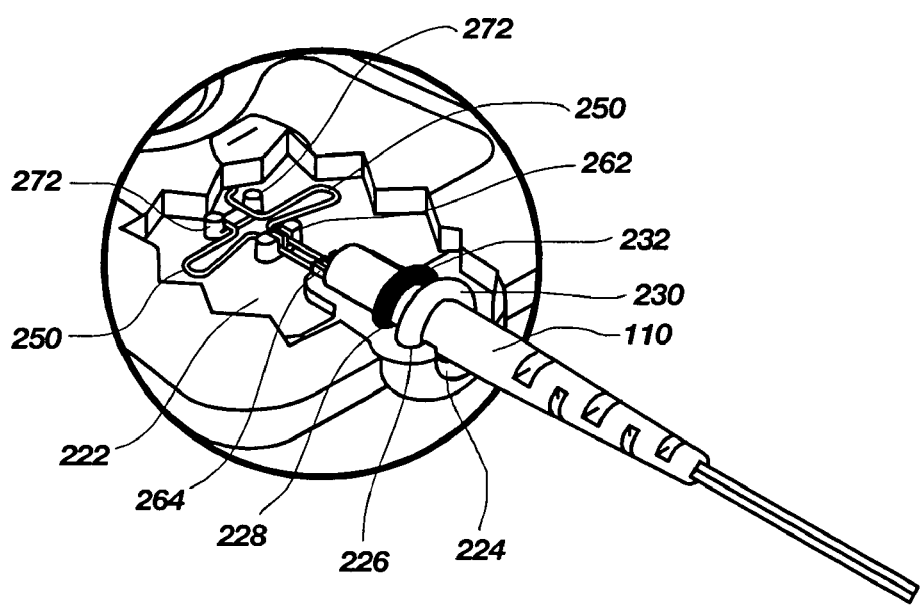
FIG. 5B is an enlarged, partial cutaway perspective view of the structure of FIG. 5A with a connector as depicted in FIG. 4 engaged therewith.
Figure 6:
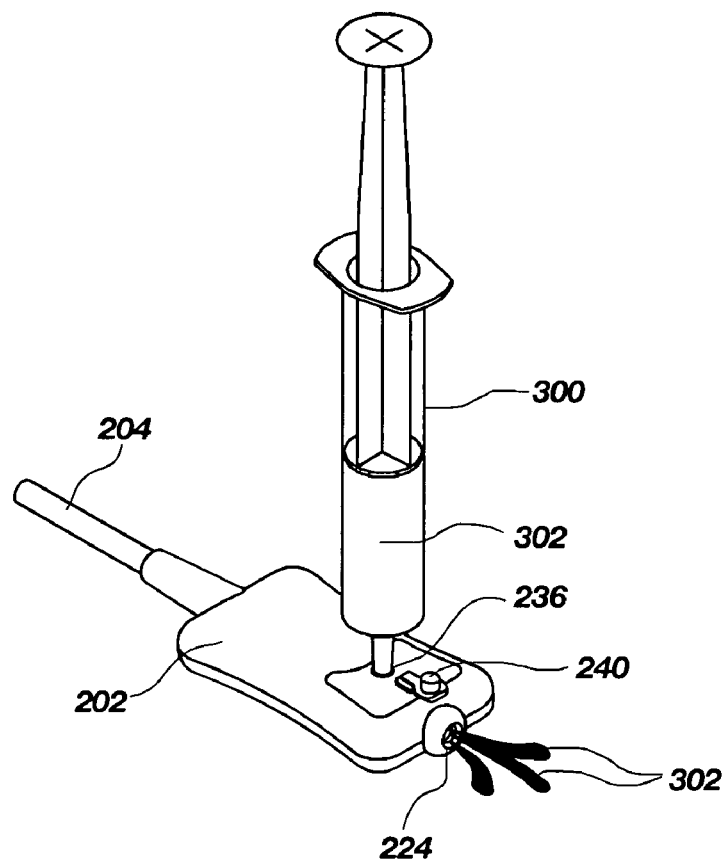
FIG. 6 is a perspective view of the housing assembly of FIG. 5 with a wash-out port thereof open and a syringe flushing a chamber of the inner housing with fluid.

FIGS. 5A and 5B depict the insertion of a connector 110 into housing assembly 202 and, specifically, into aperture 224 of inner housing 216. FIG. 6 depicts the flushing of debris from chamber 222 of inner housing 216 with fluid 302 from a syringe 300 through aperture 236 after removal of plug 240, the fluid 302 exiting chamber 222 from aperture 224.

Figure 7:
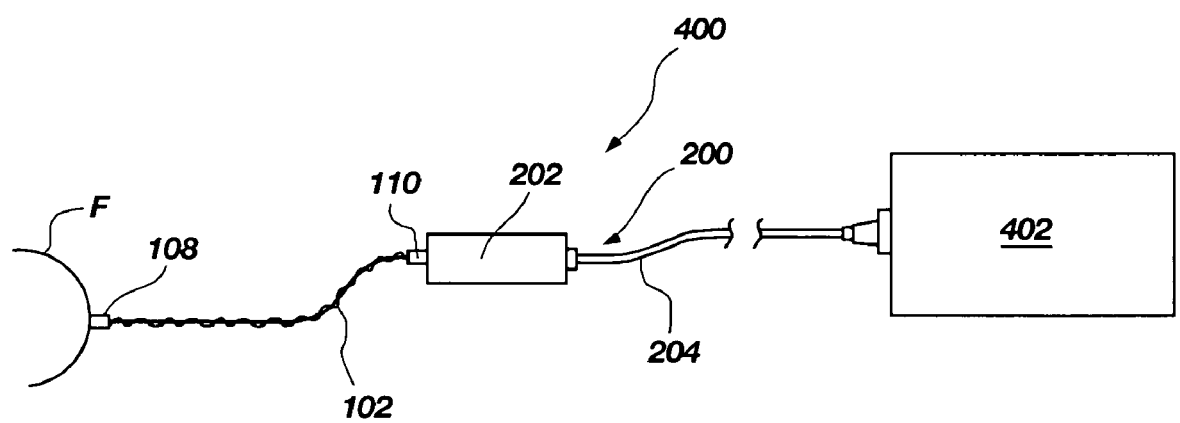
FIG. 7 is a schematic of an exemplary fetal heart rate monitoring system including a fetal heart rate electrode assembly according to the present invention including a connector engaged with a housing assembly of a cable assembly, and a cable of the cable assembly extending to a fetal heart rate monitor.

FIG. 7 is a schematic depiction of a fetal heart rate monitoring system 400 according to the present invention including an electrode block 108 carrying a spiral electrode (not shown) operably coupled to the scalp of a fetus F and a reference electrode (not shown) of a fetal heart rate electrode assembly 100 connected through twisted wire pair 102 by a connector 110 to a housing assembly 202 of a cable assembly 200, housing assembly 202 in turn being connected to a suitable monitor 402 by multi-conductor cable 204. Suitable monitors include, by way of example and not limitation, the Hewlett-Packard (now Philips Medical Systems) Series 50 and the Corometrics (now General Electric Medical) Models 116-122 fetal monitors. It is further noted that system 400 may include, without limitation, any other suitable fetal heart rate electrode assembly including a connector 110 such as, for example, the aforementioned SoftBeat™ fetal scalp electrode.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. A fetal heart rate electrode assembly, comprising:
   a drive tube having a distal end and a proximal end;
   a drive knob having a bore therethrough and secured to the proximal end of the drive tube, the drive knob comprising a body having a resiliently biased stop tab extending distally therefrom at an acute angle to the body, the stop tab having a distally facing abutment and a foot extending distally thereon;
   an electrode block located at the distal end of the drive tube and of similar outer diameter thereto, the electrode block bearing a spiral electrode protruding distally therefrom and a reference electrode, each of the electrodes being connected to one end of a wire of a wire pair extending proximally through the drive tube and through the drive knob, each wire of the wire pair extending at an opposing end thereof to a connector of smaller lateral extent than an interior diameter of the drive tube, wherein the connector comprises:
      a dielectric housing bearing a central contact proximate a presenting end thereof comprising an end of a wire of the wire pair and an annular contact surrounding the central contact and electrically isolated therefrom connected to another wire of the wire pair; and
      wherein the central contact and the annular contact comprise substantially coplanar end faces perpendicular to a longitudinal axis of the connector; and
   a guide tube having a distal end and a proximal end and of greater inner diameter than an outer diameter of the drive tube, wherein a portion of the drive tube is disposed within the guide tube and the electrode block and the electrodes are disposed within the distal end of the guide tube and the proximal end of the drive tube and the drive knob extend beyond the proximal end of the guide tube;

wherein the foot of the stop tab is disposed between the drive tube and the guide tube with the distally facing abutment of the stop tab abutting a proximal end of the guide tube.

2. The fetal heart rate electrode assembly of claim 1, wherein at least one of the spiral electrode and the reference electrode comprise stainless steel plated with gold.

3. The fetal heart rate electrode assembly of claim 1, wherein the dielectric housing further comprises an annular recess extending about a substantially cylindrical exterior portion thereof and remote from the presenting end.

4. The fetal heart rate electrode assembly of claim 1, wherein the dielectric housing further comprises a skirt extending beyond the end faces of the central contact and the annular contact and defining a cavity.

5. The fetal heart rate electrode assembly of claim 1, further comprising a cable assembly for connecting to the connector, the cable assembly comprising:

a housing assembly comprising:

an inner housing defining a chamber and having an aperture extending from the chamber to an exterior of the housing assembly;

a first annular recess in the inner housing coaxially aligned with the aperture and carrying an elastomeric annular element;

a second annular recess in the inner housing coaxially aligned with the aperture and carrying a resilient annular element;

a pair of longitudinally resiliently biased pin contacts having tips at one end thereof longitudinally aligned with the aperture and positioned for contact with the end of the wire and the annular contact of the connector as inserted into the aperture, opposing ends of the pin contacts extending though a wall of the inner housing in fluid-tight sealing engagement therewith; and an outer housing of greater internal volume than the inner housing and disposed thereover, the opposing ends of the pin contacts extending into an interior portion of the outer housing outside of the inner housing; and a multi-conductor cable extending into an interior of the outer housing outside of the inner housing, a wire of the multi-conductor cable being connected to each pin contact of the pair.

6. The fetal heart rate electrode assembly of claim 5, further comprising:

a port extending from the chamber of the inner housing to an exterior of the housing assembly; and a resilient plug flexibly secured to the outer housing and disposable in the port for closure thereof.

7. The fetal heart rate electrode assembly of claim 5, further comprising alignment structure formed on at least one interior surface of the inner housing and engaged with lateral surfaces of the pin contacts for longitudinally aligning the pin contact tips.

8. The fetal heart rate electrode assembly of claim 5, wherein the pin contacts comprise stainless steel coated with gold, and further comprising a dielectric coating thereover on a medial portion thereof lying between the tips and the opposing ends thereof.

9. The fetal heart rate electrode assembly of claim 1 further comprising a cable assembly for connecting to the connector, the cable assembly comprising:

a housing assembly comprising:

an inner housing defining a chamber and having an aperture extending from the chamber to an exterior of the housing assembly;

a plurality of contacts each having structure at one end thereof operably associated with the aperture and positioned for contact with the end of the wire and the annular contact of the connector as inserted into the aperture, opposing ends of the contacts extending through a wall of the inner housing in fluid-tight sealing engagement therewith; and an outer housing of greater internal volume than the inner housing and disposed thereover, the opposing ends of the contacts extending into an interior portion of the outer housing outside of the inner housing;

a multi-conductor cable extending into an interior of the outer housing outside of the inner housing, a wire of the multi-conductor cable being connected to an opposing end of each contact of the plurality;

a port extending from the chamber of the inner housing to an exterior of the housing assembly; and a resilient plug flexibly secured to the outer housing and disposable in the port for closure thereof.

10. A fetal heart rate electrode assembly, comprising:

a drive tube having a distal end and a proximal end;

a drive knob having a bore therethrough and secured to the proximal end of the drive tube, the drive knob comprising a body having a resiliently biased stop tab extending distally therefrom at an acute angle to the body, the stop tab having a distally facing abutment and a foot extending distally thereon;

an electrode block located at the distal end of the drive tube and of similar outer diameter thereto, the electrode block bearing a spiral electrode protruding distally therefrom and a reference electrode, each of the electrodes being connected to one end of a wire of a wire pair extending proximally through the drive tube and though the drive knob, each wire of the wire pair extending at an opposing end thereof to a connector of smaller lateral extent than an interior diameter of the drive tube, wherein the connector comprises:

a dielectric housing having an annular recess in a substantially cylindrical exterior portion thereof remote from a presenting end thereof, the dielectric housing bearing a central contact proximate a presenting end thereof comprising an end of a wire of the wire pair and an annular contact surrounding the central contact and electrically isolated therefrom connected to another wire of the wire pair; and wherein the central contact and the annular contact comprise substantially coplanar end faces perpendicular to a longitudinal axis of the connector;

a guide tube having a distal end and a proximal end and of greater inner diameter than an outer diameter of the drive tube, wherein a portion of the drive tube is disposed within the guide tube and the electrode block and the electrodes are disposed within the distal end of the guide tube and the proximal end of the drive tube and the drive knob extend beyond the proximal end of the guide tube;

wherein the foot of the stop tab is disposed between the drive tube and the guide tube with the distally facing abutment of the stop tab abutting a proximal end of the guide tube; and a cable assembly, including:
  a housing assembly comprising:
    an inner housing defining a chamber and having an aperture extending from the chamber to an exterior of the housing assembly;
    a first annular recess in the inner housing coaxially aligned with the aperture and carrying a elastomeric annular element sized for resilient, sliding engagement with the substantially cylindrical exterior portion of the dielectric housing of the connector when received within the aperture;
    a second annular recess in the inner housing coaxially aligned with the aperture and carrying a resilient annular element sized for protrusion into the annular recess of the substantially cylindrical exterior portion of the dielectric housing of the connector when received within the aperture;
    a pair of longitudinally resiliently biased pin contacts having tips at one end thereof longitudinally aligned with the aperture and positioned for contact with the end faces of the connector when received in the aperture, opposing ends of the pin contacts extending though a wall of the inner housing in fluid-tight sealing engagement therewith; and
    an outer housing of greater internal volume than the inner housing and disposed thereover, the opposing ends of the pin contacts extending into an interior portion of the outer housing outside of the inner housing; and
  a multi-conductor cable extending into an interior of the outer housing outside of the inner housing, a wire of the multi-conductor cable being connected to each pin contact of the pair.

11. The fetal heart rate electrode assembly of claim 10, further comprising:
  a port extending from the chamber of the inner housing to an exterior of the housing assembly; and
  a resilient plug flexibly secured to the outer housing and disposable in the port for closure thereof.

12. The fetal heart rate electrode assembly of claim 10, further comprising alignment structure formed on at least one interior surface of the inner housing and engaged with lateral surfaces of the pin contacts for longitudinally aligning the pin contact tips.

13. The fetal heart rate electrode assembly of claim 10, wherein the pin contacts comprise stainless steel coated with gold, and further comprising a dielectric coating thereover on a medial portion thereof lying between the tips and the opposing ends thereof.

14. The fetal heart rate electrode assembly of claim 10, further comprising:
  a monitor operably coupled to wires of the multi-conductor cable.

15. The fetal heart rate electrode assembly of claim 14, further comprising:
  a port extending from the chamber of the inner housing to an exterior of the housing assembly; and
  a resilient plug flexibly secured to the outer housing and disposable in the port for closure thereof.

16. The fetal heart rate electrode assembly of claim 14, further comprising alignment structure formed on at least one interior surface of the inner housing and engaged with lateral surfaces of the pin contacts for longitudinally aligning the pin contact tips.

17. The fetal heart rate electrode assembly of claim 14, wherein the pin contacts comprise stainless steel coated with gold, and further comprising a dielectric coating thereover on a medial portion thereof lying between the tips and the opposing ends thereof.

* * * * *